(12) United States Patent
Abazajian

(10) Patent No.: US 6,515,193 B2
(45) Date of Patent: Feb. 4, 2003

(54) PROCESS FOR PRODUCTION OF HIGHER LINEAR INTERNAL OLEFINS FROM BUTENE

(76) Inventor: Armen Nazar Abazajian, 1806 Peach Brook Ct., Houston, TX (US) 77062

( * ) Notice: Subject to any disclaimer, the term of this patent is extended or adjusted under 35 U.S.C. 154(b) by 0 days.

(21) Appl. No.: 09/828,771

(22) Filed: Apr. 9, 2001

(65) Prior Publication Data

US 2002/0183579 A1 Dec. 5, 2002

(51) Int. Cl.[7] .............................. C07C 6/04; C07C 6/02; C07C 5/25
(52) U.S. Cl. ...................... 585/644; 585/646; 585/644; 203/DIG. 6
(58) Field of Search .................................. 585/644, 646, 585/664; 203/DIG. 6

(56) References Cited

U.S. PATENT DOCUMENTS 3,600,456 A * 8/1971 Bradshaw .................... 585/647
4,709,115 A * 11/1987 Jung et al. ................... 585/643

* cited by examiner

Primary Examiner—Thuan D. Dang
(74) Attorney, Agent, or Firm—Parks & Associates P.C.

(57) ABSTRACT

A process for production of higher linear internal olefins from 1- and 2-butene feedstocks in one or a series of sequential catalytic reactive distillation columns containing olefin disproportionation and olefin isomerization catalysts.

15 Claims, 1 Drawing Sheet

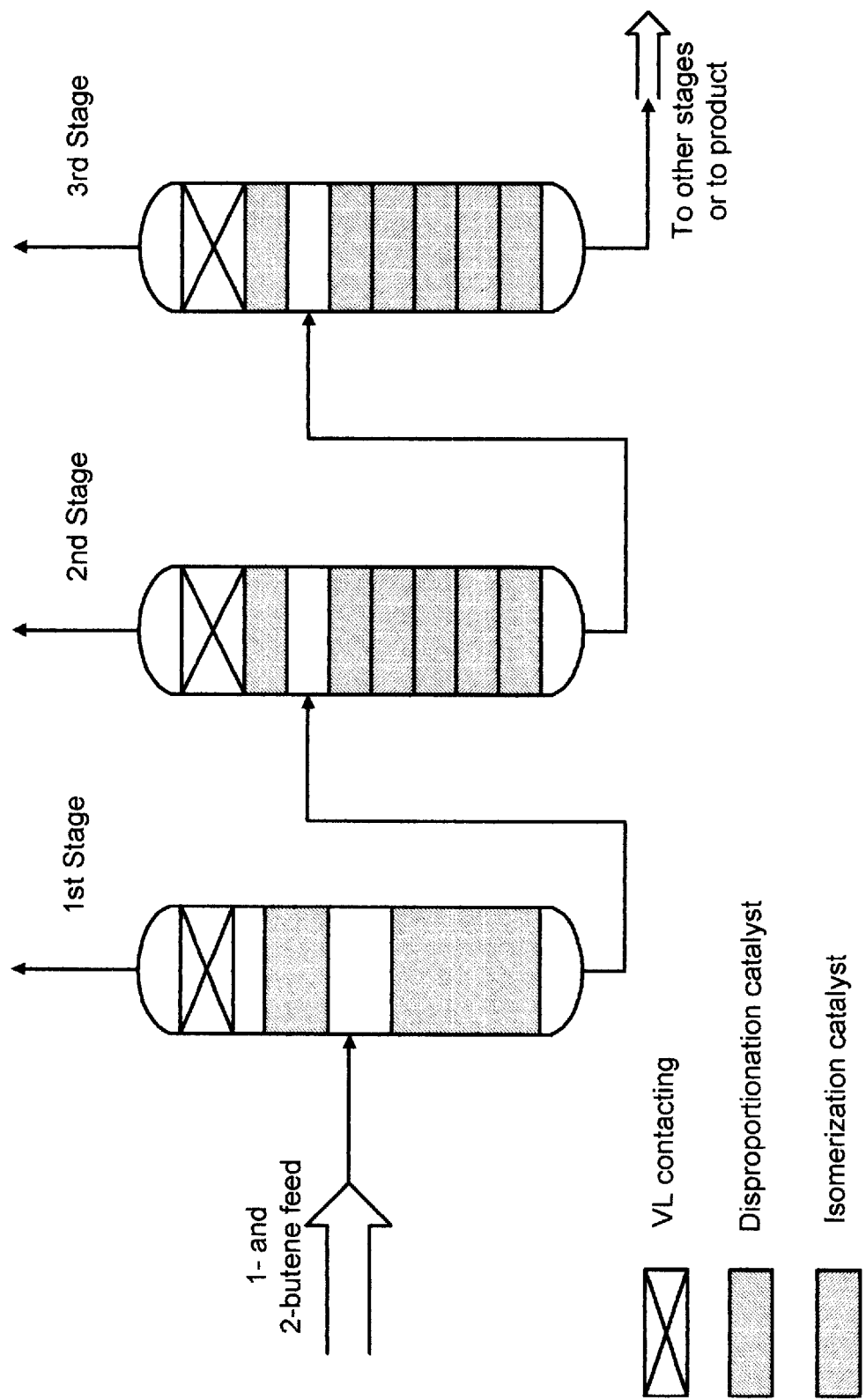

PROCESS FOR PRODUCTION OF HIGHER LINEAR INTERNAL OLEFINS FROM BUTENE

CROSS-REFERENCE TO RELATED APPLICATIONS

There are no other related applications.

STATEMENT REGARDING FEDERALLY SPONSORED RESEARCH OR DEVELOPMENT.

This research was not federally sponsored.

BACKGROUND OF THE INVENTION

The present invention relates to the production of valuable higher linear olefins from low value butenes via a catalytic disproportionation reaction in a catalytic distillation reactor.

Catalytic disproportionation, transalkylation or metathesis technology refers to the technology, which, in alkenes, exchanges the alkyl groups on both sides of the double bond with another alkene. For example, propylene can be reacted to make ethylene and 2-butene. Typically, the alkene products contain both higher and lower carbon number chains. One of the earlier examples of the prior art is described in the U.S. Pat. No. 3,261,879 (1966) regarding the reaction of propylene mentioned above. This is easily accomplished as the reactions are reversible and proceed to equilibrium, thus if starting with butene and ethylene the reaction will proceed to about 50% conversion to propylene, while starting at propylene, the reaction will proceed to about 50% conversion to ethylene and butene. Most of the prior art describes single reactant phase reactions in a fixed bed, a fluidized bed or a moving bed where the equilibrium limits the conversion to desired alkene. Longer residence times in such systems lead to isomerization and other by-product reactions. U.S. Pat. Nos. 3,463,827 (1969); 3,448,163 (1969); 3,641,189 (1972); 3,676,520 (1972) all describe processes of disproportionation of alkenes where a Group VIB metal carbonyl catalyst associated with alumina or a rhenium heptoxide on alumina, or rhenium heptoxide on alumina with mixtures of other metals. These processes, in part, discuss the reaction of 1-butene to give ethylene and 3-hexene. Although the theoretical conversion of 1-butene to ethylene and 3-hexene is about 50%, none of the references sited above were able to approach even the theoretical conversion with high selectivity to these desired products. Some systems attempted to use high temperature to drive to higher conversion, but with considerable detriment to the selectivity of the reaction because of the increased isomerization rates as well as consecutive reactions of the reaction products.

U.S. Pat. No. 4,709,115 (1987) teaches of improving the selectivity and conversion of the reactions of 1- and 2-butene to ethylene, propylene, 2-pentene and 3-hexene by using a reactive distillation column, which uses rhenium oxide catalyst impregnated on alumina both as a catalyst and a distillation substrate to facilitate phase transfer. In this reactive distillation system the conversion is improved to 85–93% and the combined yield to ethylene and 3-hexene (or ethylene, propylene (light ends) and 2-pentene, 3-hexene (heavy ends) is improved to 79.5–89%. This result is obtained because the light reaction products are removed from the liquid phase immediately and thus push the equilibrium to the heavy products. Also, this invention claims the ability to achieve high reaction rates at moderate (50–130° C.) temperatures. However, the products of this reaction are commercially insignificant, because ethylene and propylene are in general less valuable than 1-butene. 2-Pentene and 3-hexene, comprising most of the product weight, do not have valuable commercial outlets. Thus this art does use plentiful and low value feedstocks, but does not make desirable range linear internal olefin products.

U.S. Pat. 5,243,120 (1993) as well as other U.S. Pat. Nos. (3,786,112; 5,043,520; 4,996,386; and 4,180,524) all describe methods of improving yields of medium-range olefins by reacting a high carbon number chain olefin with a low carbon-number chain olefin by affecting simultaneous disproportionation and isomerization of the olefins. Most of the subject matter of these patents refers to the production of detergent-range linear internal ($C_{10}$–$C_{16}$) olefins from a feedstock of light ($C_4$–$C_8$) and heavy ($C_{18}$–$C_{20+}$) alpha-olefins. Some variation of these processes is a part of current commercial linear alcohols process. These patents advise that physical mixtures of olefin disproportionation catalyst (such as rhenium oxide) and an olefin (double bond) isomerization catalyst (such as potassium on alumina) are able to effectively simultaneously isomerize the double bond initially located in a primary position to a deep internal position and to disproportionate the light olefins with the heavy olefins, thus making a high yield of intermediate olefins Without isomerization, the mixture would tend to make ethylene and very heavy olefin. The process is conducted in a fixed bed reactor. The disadvantage of this process is that it has to use high-value light alpha-olefins and high-value heavy alpha-olefins to produce intermediate olefins of similar value. Thus this art produces some of the high-value higher olefins, but at the expense of consuming other high-value olefins and does not utilize low value feedstocks.

BRIEF SUMMARY OF THE INVENTION

This invention is a process for production of high-value higher olefins from low-value mixed 1- and 2-butene streams via olefin disproportionation in one or in more than one sequential catalytic distillation reactors. The reactor has several catalyst beds in a sequence. The various catalyst beds are: olefin disproportionation catalyst bed, including molybdenum, tungsten, rhenium elements, compounds and mixtures thereof, optionally including cobalt; olefin isomerization catalyst bed, including sodium, potassium, rubidium, cesium elements, compounds and mixtures thereof, and a bed consisting of a physical mixture of olefin disproportionation and olefin isomerization catalysts. The products of this reaction system are ethylene, propylene and some 2-butene (overhead product) and $C_5$–$C_{20}$ and higher linear internal olefins (bottoms product). This invention improves the art of disproportionation of alkyls by devising a high-yield method of producing a desirably broad range of high-value linear internal olefins from low-value 1- and 2-butenes.

BRIEF DESCRIPTION OF THE SEVERAL VIEWS OF THE DRAWING

FIG. 1. Linear Internal Olefins Process.

This drawing depicts a process consisting of several stages of physically separate reactive distillation columns.

DETAILED DESCRIPTION OF THE INVENTION

Olefins, which can serve as feedstocks to this process, are acyclic alkenes with at least two carbon atoms. Alkenes having 3 to 30 carbon atoms and mixtures of such are preferred. More specifically, mixtures of 1- and 2-butenes are the best feedstocks.

The reactor or reactors include known olefin disproportionation catalysts, such as molybdenum, tungsten and rhenium metals and their oxides, optionally including cobalt, supported on porous substrate. For the purposes of the present invention the preferred disproportionation catalyst is that containing tungsten or rhenium oxides on a porous alumina or silica-containing support. The preferred substrate is the catalytic grade gamma-alumina or silica-alumina.

Also, the reactor or reactors include known olefin isomerization catalysts, consisting of sodium, potassium, rubidium, cesium and mixtures thereof. These metals are impregnated on alumina or silica-containing porous substrate. It is preferred to calcine these impregnated metals to oxides. Further, gamma-alumina or silica-alumina is the preferred substrate for this catalyst.

The disproportionation catalyst mixture can be prepared by any of the conventional methods, including dry-mixing, impregnation or co-precipitation. One of the methods, which can be used is the impregnation of the alumina with a solution containing aqueous salts of rhenium or rhenium oxide and/or tungsten or tungsten oxide. Alumina support can be in a form of conventional dumped distillation packing, such as saddles, rings, spheres to enhance mass transfer during fractionation. After impregnation, the catalyst should be calcined at 300° C. to 700° C. in a flow of air and/or nitrogen to activate the catalyst. The disproportionation catalyst typically contains 5 to 20% by weight rhenium or 5 to 35% tungsten.

The olefin isomerization catalyst can be prepared by impregnating an alumina support with an alkali metal such as sodium, potassium, rubidium or cesium. For impregnation various salts and compounds of these metals can be used. For example, carbonates, chelates, hydroxides, alkoxylates and other compounds can be used as long as they can be decomposed to leave some form of metal oxides or aluminates on the surface. The preferred metals for this process are potassium carbonates or potassium carboxylates. After impregnation, the catalyst is calcined at 400° C. to 800° C. in the presence of air flow to activate the catalyst. Preferably, calcination temperature should be between 500° C. and 700° C. The content of an alkali metal on the alumina should be from 5 to 20% by weight.

The reactive distillation column or columns used in this process is a distillation column or columns of the following construction (See FIG. 1): the uppermost several stages of the column consists of structured low-temperature packing. The packing immediately above and/or below the feed point consists of olefin disproportionation catalyst arranged in one or several beds. Preferably, the olefin disproportionation catalyst is used in one bed immediately below the feed and in one bed immediately above the feed. The lowermost internals of the column consist of one to several beds of olefin disproportionation and olefin isomerization catalyst either physically mixed in a single bed, or arranged in alternating series of beds. The preferred method is to either physically mix the two catalysts or alternate shallow beds. Preferably, the method of alternation is isomerization/disproportionation/isomerization/disproportionation, etc. Also, the column may be separated into different physical units as the practical considerations of the unit size, optimum cost and better vapor and liquid equilibria dictates. For example, the initial reaction of 1- and 2-butene to make 2-pentene and 3-hexene over disproportionation catalyst without the presence of isomerization catalyst may be done in a separate reactive distillation column. Also, due to the limitations of vapor-liquid equilibrium, the successively higher linear internal olefins may be achieved in separate reactive distillation columns operating at successively lower pressure and higher temperature to achieve the vaporization of the successively heavier products. Also, the separation of ethylene and propylene may be done in a separate unit to reduce the temperature range handled in a single piece of equipment.

The process temperature in the column will depend on the feedstock olefin and the desired product distribution. In general, the temperature range will be between −30° C. overhead and 300° C. bottoms temperatures. Preferably, the temperatures will range between 0° C. and 200° C. The pressure in the column will also depend on the feedstock olefin and the desired extent of reaction as well as the required process temperature to achieve the desired conversion and selectivity. The pressure in the column can be 0 to 500 psia and more preferably, from 0 to 150 psia.

Three simultaneous unit operations are carried out in the reactive distillation reactor. They are: olefin disproportionation, olefin isomerization and fractionation. Feed, containing 1- and 2-butene, undergoes disproportionation in the olefin disproportionation beds located near the feed point. Depending on the feed composition, the likely products are 3-hexene, 2-pentene, ethylene and propylene. Ethylene and propylene are fractionated overhead where they are recovered. 3-hexene and 2-pentene descend lower in the column until they reach the beds containing both isomerization and disproportionation catalysts. Alternatively, in a multiple column scheme, 3-hexene and 2-pentene are collected off the bottoms of the column and fed to the next column which is packed with a mixture of both disproportionation and isomerization catalyst. In these beds 3-hexene is isomerized to a thermodynamic equilibrium mixture of 1-, 2- and 3-hexene. Subsequent disproportionation reactions of 2-hexene with itself or with 2-pentene make 4-octene or 3-heptene. These species, in turn, are isomerized partially to 2- and 3-octene, which go on to make, in par 6-dodecene, 5-undecene and 5-decene. Some of this is accomplished in the same physical reactive distillation column, while for best results the mixture with the average composition of between heptene and octene can be removed and fed to a subsequent reactive distillation column. The advantage of the reactive distillation scheme is that at any point in the reactor the light species are flashed off thus preventing the recombination of the products back to the reactants. The fractionation of the lights concentrates the heavies and assures the building of the longer molecules in the lower beds of the column. The butene will be bottled up in the column and mostly reacted to either to lights or to heavies, while some is distilled overhead and, if it is warranted, recycled. Pentene, as well, not being a desirable product, will be reacted to extinction in the reactive distillation columns. Alternatively, unreacted butene and pentene may be dropped out of the bottoms of the column when a particularly light product distribution is desired. Depending on the vapor liquid equilibrium present in the reactive distillation column, the bottoms product will consist of a range of products in a bell-curve, Poisson or modified or skewed bell-curve or Poisson distribution.

EXAMPLE 1

The first stage of the system to manufacture linear internal olefins from 1- and 2-butenes consists of a reactive distillation column packed with disproportionation catalyst only. The product of this stage, whether in-situ in the same physical vessel, or in a different physical vessel is a mixture of pentenes and hexenes. These pentenes and hexenes are then fed into the second stage, where there is both the transalkylation and isomerization catalyst is present as described above.

The reaction conditions were:

Overhead pressure: 30 psig; reboiler temperature: 300° F.

The composition of the bottoms of the reactive distillation in weight percent (wt %) was:

$C_4$ 8.15
$C_5$ 46.21
$C_6$ 26.92
$C_7$ 13.31
$C_8$ 1.69

EXAMPLE 2

The product from the first stage as described in Example 1 was introduced into the second stage at slightly different conditions. The conditions were:

Overhead pressure=20 psig, reboiler temperature=400° F.
The second stage bottoms composition in wt % was:
$C_6$ 3.1
$C_7$ 18.3
$C_8$ 61.7
$C_9$ 13.2
$C_{10}$ 2.5
$C_{11}$ 1.1

EXAMPLE 3

The product from the first stage as described in Example b 1was introduced into the second stage at slightly different conditions. The conditions were:

Overhead pressure=20 psig, reboiler temperature=350° F.
The second stage bottoms composition in wt % was:
$C_5$ 4.7
$C_6$ 38.5
$C_7$ 38.2
$C_8$ 18.6

EXAMPLE 4

The product from the second stage as described in Examples 1–3 was introduced into the third stage also containing layered transalkylation and isomerization catalysts. The conditions were:

Overhead pressure=10 psig, reboiler temperature=400° F.
The third stage bottoms composition in wt % was:
$C_8$ 3.77
$C_9$ 20.16
$C_{10}$ 34.97
$C_{11}$ 25.1
$C_{12}$ 10.37
$C_{13}$ 3.87
$C_{14}$ 2.16
$C_{15}$ 0.59

EXAMPLE 5

The product from the second stage as described in Examples 1–3 was introduced into the third stage also containing layered transalkylation and isomerization catalysts. The conditions were:

Overhead pressure=10 psig, reboiler temperature 450° F.
The third stage bottoms composition in wt % was:
$C_7$ 0.2
$C_8$ 1.9
$C_9$ 6.6
$C_{10}$ 16.4
$C_{11}$ 23.5
$C_{12}$ 21.4
$C_{13}$ 14.3
$C_{14}$ 8.2
$C_{15}$ 4.2
$C_{16}$ 2.0
$C_{17}$ 0.9
$C_{18}$ 0.4

The yield to heavy products ($C_6$ and heavier) is thought to be in the range of 20% to 80% by weight, more preferably 50% to 75% by weight. Most preferably, the yield to heavy products will be about 70% by weight. The product distribution can be controlled by varying temperature and pressure in the columns.

What I claim as my invention is:

1. A process for producing heavy linear internal olefins from 1- and 2-butene feedstocks in successive stages in a reactive distillation column or in stages in successive sets of reactive distillation columns having tops and bottoms employing disproportionation catalysts containing rhenium, tungsten or molybdenum elements and isomerization catalyst containing sodium, potassium, rubidium, cesium and mixtures thereof comprising;

reacting, as a first stage, said 1- and 2-butene in the presence of only said disproportionation catalyst at an operating temperature and pressure for disproportionation;

reacting, as at least a second stage, in the presence of a mixture of disproportionation catalyst and isomerization catalysts said 1- and 2-butene reacted in said first stage at a second operating temperature and pressure disproportionation and isomerization thereof to produce lighter and heavier species therefrom;

lowering progressively said operating pressure in said reactive distillation column from said pressure of said first stage in said reactive distillation column;

maintaining said operating temperature at said first stage temperature to at least said second operating temperatures in said at least second reacting stage;

removing said light species as vapor from said reactive distillation column; and reacting said heavier species with said heavier species for producing heavy linear internal olefins.

2. The process of claim 1 wherein said process of reacting, as at least a second stage in the presence of a mixture of disproportionation catalyst and isomerization catalysts further comprises reacting as at least a third successive stage said heavier species in the presence of said mixture of disproportionation and isomerization catalysts at progressively lower pressures and at least at said same temperatures in said at least second stage for producing heavier linear internal olefins.

3. The process of claim 2 wherein said mixture of isomerization and disproportionation catalysts is a physical mixture of said catalysts provided in alternating layers of catalysts.

4. The process of claim 2 wherein said temperatures and pressures in said reacting as said first stage said 1- and 2-butene only in the presence of said disproportionation catalyst further comprises operating pressures of from 0 to 200 psia and operating temperatures at said bottoms from 100 to 500 F. for formation of species 2-pentene and 3-hexene at said reacting, as said first stage.

5. The process of claim 4 wherein 2-pentene and 3-hexene are reacted, as at least a second stage in the presence of a mixture of isomerization catalysts and disproportionation catalyst at said second operating pressures of 0–100 psia, and at said second operating temperatures at said bottoms from 100 to 600 F. for the production of a range of heavier linear internal olefins C4 through C20 but predominantly hexene, heptene, octene, nonene and decene.

6. The process of claim 5 wherein heavier internal olefins from said heavier species hexene, heptene, octene, nonene, and decene from said range of heavier linera internal olefins C4 through C20 are reacted, as at least a third stage in the presence of a mixture of isomerization catalysts and disproportionation catalyst at 0–100 psia pressure, and 100–600 F temperature at said bottoms for the production of linear infernal olefin products form C4 to C20 but predominantly C5 through C11.

7. The process of claim 6 wherein said progressively heavier species C5 through C11 from said range of heavier linear internal olefins C4 to C20 are reacted, as at least a fourth stage in the presence of a mixture of isomerization catalysts and disproportionation catalyst at 014 100 psia and 100–600 F. temperatures at said bottoms, for the production of C5–C30 linear internal olefins but predominantly C8–C25 linear internal oleinfs.

8. The process of claim 5 wherein the yield of said heavy internal olefins by weight is 70%.

9. The process of claim 2 wherein said mixture of isomerization and disproportionation catalysts is a physical mixture of said catalysts provided in alternating beds.

10. The process according to claim 1 wherein said operating temperatures of each of said stages are between −30 C. at said tops and 300 C. at said bottoms of said reactive distillation column.

11. The process according to claim 10 wherein said operating temperatures are between 0 C. at said tops and 200 C. at said bottoms of said reactive distillation column.

12. The process according of claim 1 wherein the operating pressure are between 0 psia at said tops and 500 psia at said bottoms of said reactive distillation column.

13. The process according to claim 12 wherein said operating pressures are between 5 psia at said tops and 100 psia at said bottoms of said reactive distillation column.

14. The process of claim 1 wherein the overall yield of said heavier internal olefins by weight is 30% to 80%.

15. The process of claim 1 wherein said feedstock composition of said 1-butene and 2-butene is from at least trace amounts of 1-butene to at least trace amounts of 2-butene and the balance being said other butene.

* * * * *